United States Patent [19]

Hammond

[11] Patent Number: 4,965,047
[45] Date of Patent: Oct. 23, 1990

[54] ANALYTICAL TEST STRIP

[75] Inventor: John M. Hammond, Wantage, England

[73] Assignee: CMB Foodcan p.l.c., England

[21] Appl. No.: 156,837

[22] Filed: Feb. 17, 1988

[30] Foreign Application Priority Data

Feb. 17, 1987 [GB] United Kingdom ............... 8703578
Nov. 23, 1987 [GB] United Kingdom ............... 8727369

[51] Int. Cl.⁵ .................... G01N 31/22; G01N 21/00
[52] U.S. Cl. ................................. 422/58; 422/56; 422/57; 422/61
[58] Field of Search .............. 422/58, 57, 56, 61, 422/86, 87, 88; 436/805

[56] References Cited

U.S. PATENT DOCUMENTS

| 29,725 | 8/1860 | Johnson et al. | |
|---|---|---|---|
| 2,785,057 | 3/1957 | Schwab et al. | 422/58 |
| 3,741,727 | 6/1973 | Stroterhoff | 422/68 |
| 3,884,641 | 5/1975 | Kraffczyk et al. | 422/58 |
| 3,915,647 | 10/1975 | Wright | 422/70 |
| 4,007,010 | 2/1977 | Woodbridge, III | |
| 4,040,515 | 8/1977 | Hessel et al. | |
| 4,042,336 | 8/1977 | Larsson | 422/58 |
| 4,110,079 | 8/1978 | Schaeffer et al. | 422/56 |
| 4,428,907 | 1/1984 | Heijenga et al. | 422/61 |
| 4,522,923 | 6/1985 | Deutsch et al. | 436/536 |
| 4,857,453 | 8/1989 | Ullman et al. | 435/7 |

FOREIGN PATENT DOCUMENTS

| 453286 | 10/1970 | Australia . |
| 8615245 | 7/1986 | Fed. Rep. of Germany . |
| 3515420 | 10/1986 | Fed. Rep. of Germany . |
| 8606488 | 11/1986 | PCT Int'l Appl. . |
| 1331503 | 9/1973 | United Kingdom . |
| 2002316 | 2/1979 | United Kingdom . |

Primary Examiner—Robert J. Warden
Assistant Examiner—Thalia P. Vassilatos
Attorney, Agent, or Firm—St. Onge Steward Johnston & Reens

[57] ABSTRACT

An analytical test strip has a flexible blister (12) thermoformed in a sheet plastics member (22), and a diaphragm (34) which closes the blister to create a reservoir for holding a reagent and/or carrier liquid (32). The sheet plastics member (22) is further formed with one or two spikes (28) the or each of which is disposed within the blister and extends in a reentrant manner towards the diaphragm where it terminates at a point. For use of the dispenser the blister is pinched by finger pressure applied by the user to cause the spike or spikes to puncture the diaphragm and release the reagent and/or carried liquid which then soaks along an absorbent layer (40) until it reaches a viewing window (20). The test substance, particularly a liquid, is applied to the absorbent layer at a cavity (16), and combines with the reagent and/or carrier liquid as it moves to the viewing window. If required, the absorbent layer may include one or more discrete areas or bands (44) of an absorbed reagent substance through which the reagent and/or carrier liquid and the test substance pass. The medical (or other) condition for which the test is being made is shown as a color or tone change of the absorbent layer as seen through the viewing window.

20 Claims, 3 Drawing Sheets

ANALYTICAL TEST STRIP

This invention relates to analytical test strips, that is to say, to analytical devices of the kind which are generally in elongate strip-like form and have an area or region adapted to receive a quantity of a substance of which a medical or other condition is required to be determined. The presence or absence of the condition, or its degree, is then indicated by a colour or tone change of a part of the device. Usually, although not necessarily, the substance to be tested is a liquid.

Some analytical tests which are performed on a test substance require that a substantial quantity of a liquid should be freely available for the purposes of the test, for reaction with the test substance and/or with another reagent, and/or in order to act as a carrier medium. Hitherto, no practical way known to Applicants has been found of providing an analytical test strip with a reservoir for such a liquid, without compromising the inherent convenience of use of the strip, its compact and readily transportable nature and/or its relative cheapness. By employing the present invention, however, an analytical test strip can be provided with a reservoir of a reagent and/or carrier liquid which can be readily accessed when desired and yet which does not involve these compromises, or only to a limited degree.

Accordingly the invention provides, from one aspect thereof, an analytical test strip, which has a layer of absorbent material with which a test substance may be brought into contact and along which a test substance and one or more reagent and/or carrier liquids may pass together to a viewing window or region so as to indicate a predetermined condition of the test substance as a colour or tone change visible at the viewing window or region, for holding at least one of the reagent and/or carrier liquids the test strip having a liquid impermeable but deformable blister and a liquid impermeable but rupturable diaphragm closing the blister with the said reagent or carrier liquid therein, there being provided at least one spike which is disposed within the blister and extends from the blister to a free end adjacent the diaphragm, the diaphragm being rupturable by the or each spike on deformation of the blister, such rupturing allowing the reagent and/or carrier liquid to leave the blister through the opening formed thereby in the diaphragm, and thence to move into contact with the absorbent layer.

Preferably the blister and the or each spike are formed in a plastics enclosure of the strip. Advantageously, the plastics enclosure is formed by two sheet plastics members which are peripherally sealed together, the blister and the or each spike being formed in one of the sheet plastics members by a thermoforming operation.

In a particularly advantageous form of the invention the blister has two spikes located in spaced relation and arranged so as each to rupture the diaphragm on deformation of the blister. Preferably with such an arrangement the blister has an outwardly convex top from which the spikes are carried, the top requiring inversion for causing the spikes to rupture the diaphragm, and thereafter remaining permanently in its inverted condition.

These and other aspects and features of the invention will become apparent from the following description of embodiments thereof, now to be described by way of example and with reference to the accompanying drawings.

Detailed Description of the Preferred Embodiment(s).

Figures 1, 2:
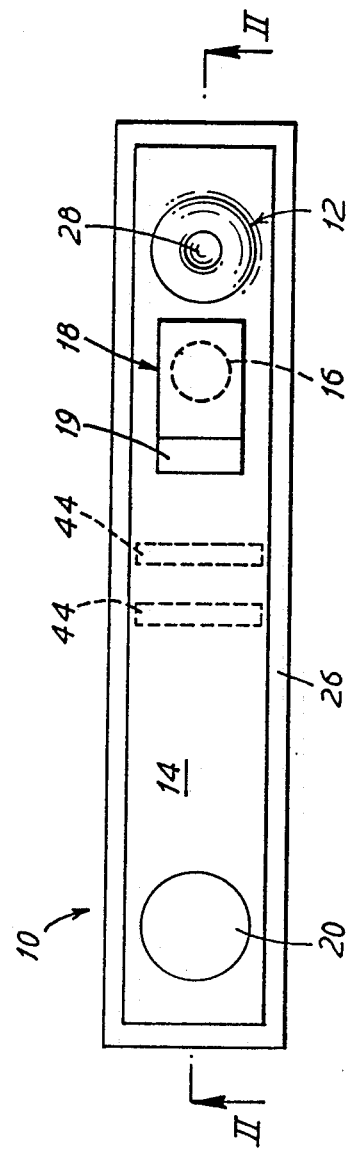
FIG. 1 is a diagrammatic plan view of a first analytical test strip in accordance with the invention.
FIG. 2 is a foreshortened view of the first test strip as seen in sectional side elevation taken on the line II—II of FIG. 1 and to an enlarged scale.

Referring firstly to FIGS. 1 and 2, a test strip 10 for medical diagnosis or other analytical test is elongate and rectangular and typically has dimensions 80 mm long × 10 mm wide by 3 mm deep. It has a reservoir for a reagent and/or carrier (e.g. solvent) liquid having the form of a blister 12 which projects from the upper surface 14 of the strip adjacent one end of the latter, the right hand end as shown.

Closely adjacent the blister 12 between the blister and the other end of the strip the upper surface 14 is formed with a shallow cavity 16 in which a drop or drops of a liquid to be tested may be placed by a pipette or the like.

A removable, adhesively or otherwise bonded (e.g. heat-sealed) protective patch 18 closes the cavity 16 to maintain sterility to the point of use, at which time it is peeled away by the user to reveal the cavity beneath. A free (unbonded) finger grasping portion 19 of the patch facilitates removal.

A window 20 is provided at the end of the strip remote from the blister 12, through which an underlying liquid-absorbent layer of the strip may be viewed as will later be understood.

The structure of the test strip is shown in FIG. 2, in which it will be seen that the blister 12 is integrally formed in a plastics member 22 providing the upper surface 14 of the strip.

The member 22 is formed from a suitable transparent or translucent plastics sheet material such as unpigmented poly vinyl chloride (P.V.C.) sheet; in addition to the blister the sheet material is formed with a hole which is cut through the sheet material to form the cavity 16.

The member 22 is plane, with the exception of the blister 12 and of a shallow downturned peripheral wall 24 which is terminated by a plane heat-seal flange 26. The wall 24 and terminal flange 26 extend continuously around the test strip. The member 22, with its blister 12, wall 24 and flange 26, is conventionally formed from the plastics sheet material by a thermoforming operation.

The blister 12 is generally rounded and approximately part-spherical. It is centrally formed by the thermoforming operation with a hollow spike 28 extending in a reentrant manner into the interior of the blister so as to terminate at a relatively sharp point which is located just short of the plane undersurface 30 of the member 22 within the confines of the wall 24.

As previously mentioned, the blister 12 forms a reservoir for the reagent and/or carrier liquid, the latter being denoted in FIG. 2 by the reference numeral 32. To contain the liquid the bottom of the blister is closed by a liquid-impermeable diaphragm layer 34 which is heat-sealed to a plane annular part of the undersurface of the member 22 around the blister. The clearance 36 of the diaphragm layer from the point of the spike 28 is sufficient to prevent inadvertent operation of the device.

The diaphragm layer is rupturable and cut from a thin metal foil (e.g. aluminium) having a plastics coating to render it heat-sealable to the member 22 and to protect it against possible corrosion by the liquid in the blister. The opaque nature of this diaghragm layer material is conveniently utilised by extending the diaphragm layer so that, as shown, it occupies the whole area of the test strip within the confines of the peripheral wall 24, and by forming it with a hole to provide the viewing window 20. For the purposes of the test cavity 16, a further hole is formed in the diaphragm layer in register with the hole in the member 22.

Beneath the diaphragm layer 34 and likewise occupying the area of the test strip within the wall 24, is a relatively thick layer 40 of a suitable liquid-absorbent material, fibrous or otherwise The layer 40 is flush with the plane bottom face of the terminal flange 26 of the thermoforming 22, and is secured into position by a further layer 42 which forms a plane base for the test strip and is heat-sealed peripherally to the bottom face of the flange 26.

The base layer 42 is relatively thick and rigid, and made from a plastics sheet material a plastics-coated metal foil or a plastics-coated board. In combination, the member 22 and base layer 42 form a generally fluid impermeable enclosure or cover for the test strip and give the strip sufficient rigidity with abuse and puncture resistance to enable it to withstand normal handling loads and retain sterility to the point of use.

A preferred process for manufacturing the test strip is as follows. The member 22 is thermoformed and severed from its parent plastics sheet, the hole to form the cavity 16 being formed during the severance operation. With the thermoforming 22 supported in an inverted position, a metered amount of the reagent and/or carrier liquid 32 is charged into the blister 12 and the material to form the diaphragm layer 34 is heat-sealed to the thermoforming to enclose the liquid within the blister in a liquid-tight manner. The subassembly formed in this way can be handled as a unit and subjected to sterilisation and/or other operations as desired; also, the cover strip 18 may be added at this stage.

A precut strip of absorbent material is thereafter located in position within the wall 24 as the layer 40, and the layer 42 is heat-sealed to the flange 26 and severed from the parent sheet material from which it is formed. The test strip then is complete, and may be packaged within an outer pack or container (not shown) for transit and storage.

To use the strip the user merely has to tear away the protective patch 18 and place some of the test liquid in the cavity 16; at a time dependent, inter alia, upon the chemical reactions which are to occur within the strip, he or she grasps the strip between index finger and thumb at the blister 12, and applies pressure to the blister to deform the latter so that the spike 28 engages and pierces the diaphragm layer 34 beneath.

The liquid 32 is thereby allowed to pass from the blister and onto the absorbent layer 40, and soaks along the latter until eventually it reaches the viewing window 20 after a time delay which may be of seconds or minutes duration. In passing the cavity 16 the liquid 32 combines with the test liquid, the two liquids thereafter moving together along the absorbent layer 40 to the viewing window. Any chemical reaction between the two liquids (or their reaction, products) will occur during this time.

For some applications the test liquid, the liquid 32 and/or the reaction products ( if any) of those liquids may require to be reacted with one or more reagents. Such a reagent may conveniently be incorporated as a discrete band of absorbed liquid in the layer 40. The embodiment of FIGS. 1 and 2 has two such bands denoted by the reference numeral 44. As an alternative to the band or bands 44, the blister 12 may be internally subdivided by one or more internal walls, the one or more additional compartments so formed within the blister being individually provided with a respective spike 28 and containing a respective reagent and/or carrier liquid; the spikes 28 are operated together when the blister is pinched by the user. As a further possibility, two or more discrete blisters 12 may be provided for the test strip.

In known manner, the colour or tone of the liquid 32 or its reaction product(s) as viewed at the viewing window provides the user with a desired indication relating to the medical or other condition which is to be diagnosed from the test liquid. Alternatively, the material of the layer 40 at the viewing window may itself be sensitive to the condition, so as to change colour or tone accordingly in response to one or more of the reaction products which occur within the test strip when the condition is present. Usually, chromatographic techniques are employed and the viewing of the viewing window is done a predetermined time after the test liquid is applied and the blister is pinched.

Figure 3:
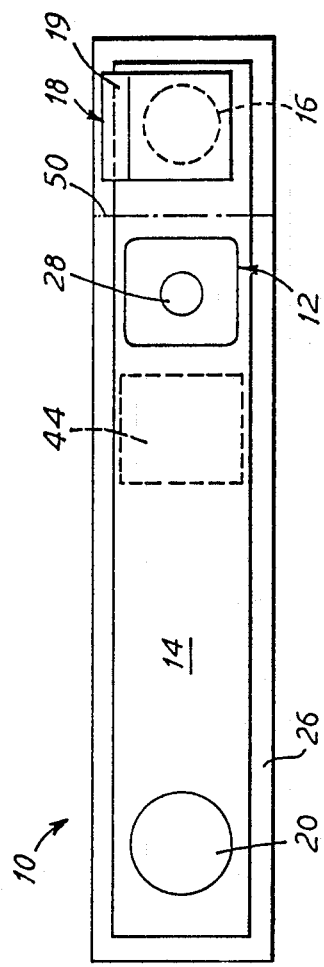
FIG. 3 is a view corresponding to FIG. 1 of a second analytical test strip in accordance with the invention.

FIG.3 shows a further test strip which can be considered as the test strip of FIGS. 1 and 2 when modified for applications in which the strip is dipped into the test liquid instead of the test liquid being applied to the test strip. In the second test strip the blister 12 (which, for space considerations is of substantially square rather than circular outline) is spaced by a substantial distance from the end opposite the viewing window 20, so as to leave an end portion (delineated in the drawing by the line 50) which can be dipped into the test liquid. At the end portion 50 the thermoformed plastics member 22 and, if appropriate, the diaphragm layer 34 are formed with a hole to provide access for the test liquid to the absorbent layer 40 beneath. As with the first embodiment, therefore, a cavity 16 is formed in the top face of the strip, and to maintain sterility to the point of use this cavity is covered by a removable cover patch 18 having a free portion 19 for finger access. For the purposes of illustration, the test strip of FIG.3 is shown to have a single reagent incorporated in the layer 40 at the square 44 of substantial area.

As an alternative to the dipping procedure of the previous paragraph, the test strip of FIG. 3 may, if desired, be used in the same manner as the test strip of FIGS. 1 and 2; thus, a drop or drops of the test liquid may be placed in the cavity 16 by a pipette.

Figure 4:
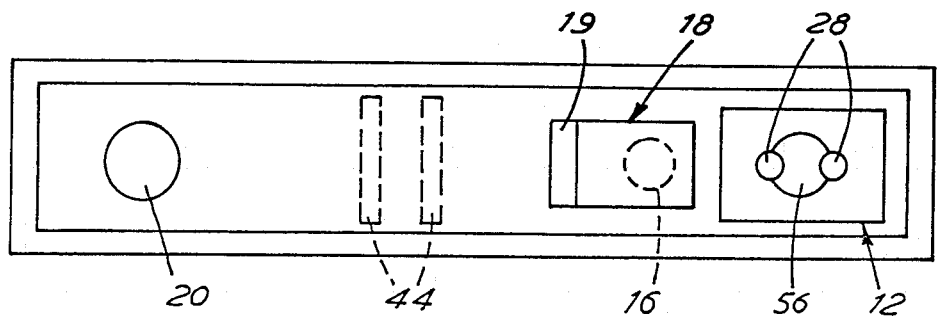
FIG. 4 is a view corresponding to FIG. 1 of a third analytical test strip in accordance with the invention.
Figure 5:
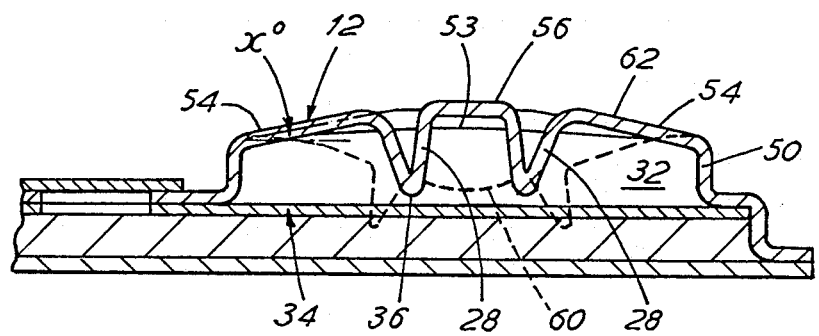
FIG. 5 is a view corresponding to FIG. 2 of the blister of the strip of FIG. 4.

FIGS. 4 and 5 show a further test strip which differs from the test strip of FIGS. 1 and 2 only in the arrangement of its blister 12. The blister is rectangular as in FIG. 3, but, in contrast with the blisters of both of the test strips described earlier, in this embodiment the blister has two spaced spikes 28. The spikes are aligned along the major axis of the blister which itself is aligned along the centreline of the strip as a whole.

As shown in FIG. 5, the blister 12 of this embodiment has an upstanding peripheral wall 50 and a domed top 62 by which the spikes 28 are carried with their tips 36 just clear of the underlying diaphragm layer 34.

The domed top 62 is attached to the peripheral wall 50 along the four upper edges of the peripheral wall, which are themselves upwardly bowed as is shown and denoted by the reference numeral 53 for the upper edge of one of the major faces of the peripheral wall.

The domed top 62 is generally of shallow frustoconical form, and intersects the four faces of the peripheral wall 50 at their upwardly domed upper edges 53. The spikes 28 are carried by the domed top, one on each side of a generally circular flat or plateau 56 which forms the centre of the domed top.

For the reason to become apparent below, the angle to the horizontal made by the domed top at its junction with the peripheral wall 50 is denoted in FIG. 5 by the letter x. The peripheral wall itself may, if desired, be inclined to the vertical upwardly and inwardly by a small angle of, typically, 5 degrees, which allows the empty thermoformings 22 to be nested together for storage and/or transit.

The spikes 28 are identical and conveniently of rightconical form. They are formed symmetrically in relation to the central transverse plane of the blister 12. Individually the spikes 28 perform the same function as the spike of each of the previous embodiments, that is to say, they puncture the underlying diaphragm layer 34 when the blister is squeezed. However, because two spaced holes are formed instead of only one, the reagent and/or carrier liquid 32 in the blister can more readily leave the blister when the latter is operated; during evacuation either hole may serve for passing the liquid onto the underlying liquid-absorbent material 40 as before, whilst the other hole is available to allow air to enter the blister in the opposite direction and so prevent any pressure reduction within the blister such as might impede or prevent the liquid from flowing. In a modification of the described arrangement the absorbent layer 40 is reduced in width in relation to, and below, the blister 12 so as to provide unoccupied chambers beneath the blister from which the replacement air can be supplied.

Operation of the blister of FIGS. 4 and 5 is essentially as previously described in relation to the previous embodiments. In this embodiment, however, the blister performs a tamper-evidence function. In order to release the reagent and/or carrier liquid as required, the user must compress the blister to the position indicated by the broken line 60 in FIG. 5, which represents the upper surface of the blister.

In moving to the position 60 the domed top 62 is inverted and passes through a horizontal, overtoggle position. When, therefore, the user subsequently releases pressure on the blister the top 62 remains stably in this inverted position and so provides subsequent evidence that the test strip has been used; furthermore, because the blister is no longer in a condition for further operation, the user cannot attempt to "pump" the liquid along the strip by repeated operation of the blister. ("Pumping", if it occurs, may cause faulty indication by the strip because of irregularity in the feeding of the liquid onto the liquid-absorbent layer 40).

Applicants have found that in order to achieve this permanent inversion of the domed top 62, the angle x° made between the domed top and the peripheral wall 50 should be at or above a predetermined angle which for the strip shown in FIGS. 4 and 5 is approximately 12 degrees. For values of x° much below this figure the domed top will always return resiliently to its initial, upwardly convex position when the blister is released; no readily apparent tamper-evidence is then available, and the user may pump the released liquid along the strip as mentioned in the previous paragraph. For some applications, however, the blister may be designed to give non-permanent inversion of its upper surface. For that purpose the blister may have a substantially plane top face.

Because of their off-centre positions on the blister 12 and the distortion which the domed top 62 of the blister undergoes during its inversion, the spikes of FIGS. 4 and 5 are caused to engage and pierce the diaphragm layer 34 with a downwardly directed, swinging motion. The holes which are made by the spikes in the diaphragm layer are therefore of elongate form and considerably larger in area than the cross-section of the spikes at their intersection with the diaphragm layer. Thus, although inversion of the domed top may cause the spikes to remain permanently inserted in the holes which they form, those holes are sufficiently large to allow the desired flows of liquid and replacement air from and to the blister.

In a modification of each of the test strips of FIGS. 1, 2 and 4, 5 as they are shown, the diaphragm layer 34 serves only to close the blister and is therefore terminated adjacent to the blister periphery; the viewing window 20 is then otherwise provided, or defined (for example) as a marked area of the member 22.

In a modification of each of the test strips as particularly described above, the liquid-absorbent layer 40 is formed with a through hole in alignment with the or each spike 28. One such hole is illustrated in FIG. 2 and indicated by the reference numeral 52. The hole 52 facilitates the rupturing of the diaphragm layer 34 by the spike when required, and then forms a small reservoir to receive and hold the reagent and/or carrier liquid 32 in intimate edge contact with the material of the layer 40. It thereby assists the wicking of the reagent and/or carrier liquid along the test strip.

Many arrangements of analytical test strip in accordance with the invention are possible other than those particularly described above. For example, in one modification of the strip of FIG. 3, no cavity 16 is provided; instead, the wall 24 and terminal flange 26 at the adjacent end of the strip are cut away to reveal the end of the absorbent layer 42; if desired, the absorbent layer 40 may project beyond the member 22 to provide a free end portion which can be dipped in the test liquid. In a further modification the test strip of FIG. 3 has its blister formed with two spikes such as are shown in FIGS. 4 and 5.

Although particularly described for testing substances which are in liquid form, the invention may have application to the analytical testing of solid, particularly pulverulent, substances.

I claim:

1. An analytical test strip comprising
   an elongated layer of absorbent material along which liquid may pass,
   upper and lower layers of liquid impermeable material sandwiching the absorbent layer therebetween, said liquid impermeable material being interrupted to enable a test substance to be brought into contact with the absorbent layer at a predetermined position therealong, and said liquid impermeable material including a viewing window through which the absorbent layer is visible for detecting a color or tone change indicating a predetermined condition of a test substance introduced at said predetermined position and having passed along the absorbent layer with one or more reagent or carrier liquids to said viewing window or region, a deformable blister defined by said liquid impermeable material in a position overlying the absorbent layer and holding at least one reagent or carrier liquid, and a liquid impermeable but rupturable diaphragm separating the blister from the absorbent layer and closing the blister with each said reagent or carrier liquid therein, said blister, said viewing window and said predetermined position for introducing the test substance being spaced apart along the test strip with said viewing window being nearest one end of the test strip, the blister having at least one integral spike formed on said liquid impermeable material and defining an inner surface portion of said blister and extending to a free end adjacent the diaphragm, whereby the diaphragm is rupturable by each spike on deformation of the blister to allow the reagent or carrier liquid to leave the blister through the opening thus formed in the diaphragm and to contact the absorbent layer.

2. A test strip as claimed in claim 1, wherein the upper and lower layers of impermeable material form a plastic enclosure of the strip.

3. A test strip as claimed in claim 2, wherein the enclosure is formed by first and second sheet plastics members which are peripherally sealed together, the blister and the or each spike being formed in the first sheet plastics member by a thermoforming operation.

4. A test strip according to claim 2, where the viewing window or region is formed by a transparent area of the enclosure, through which the absorbent layer is visible.

5. A test strip according to claim 4, wherein the material forming the diaphragm is opaque and extends from the diaphragm to and beyond the viewing window or region, the said diaphragm material being formed with an opening defining the viewing window or region.

6. A test strip according to claim 2, wherein the enclosure has an opening for the test substance to be applied to the absorbent layer, which opening longitudinally of the strip is located between the blister and the viewing window or region.

7. An analytical test strip according to claim 2, wherein the enclosure has an opening for the test substance to be applied to the absorbent layer, which opening in longitudinally of the strip is located beyond the blister in relation to the viewing window or region.

8. A test strip according to claim 2, which has an opening in the enclosure remote from the viewing window or region, the strip being arranged to be dipped into the test substance to bring the substance into contact with the absorbent layer through the said opening.

9. A test strip according to claim 6, which has the said opening thereof temporarily closed by a removable cover which is peelably adhered to the enclosure.

10. A test strip according to claim 1, wherein the absorbent layer has one or more discreet bands or regions of an absorbed reagent substance through which the reagent and/or carrier liquid and the test substance pass.

11. A test strip according to claim 1, wherein two said spikes are provided and located in spaced relation within the blister so as each to rupture the diaphragm on deformation of the blister.

12. A test strip according to claim 11, wherein the blister has an outwardly convex top from which the spikes are carried, the top requiring inversion for causing the spikes to rupture the diaphragm and thereafter remaining permanently in its inverted condition.

13. A test strip according to claim 12, wherein the blister is generally rectangular and comprises an upstanding peripheral wall, and said top is supported by said peripheral wall at upper edges thereof which are upwardly bowed.

14. A test strip according to claim 11, wherein each spike is arranged to rupture the diaphragm with a swinging motion so that the opening formed in the diaphragm by the spike is enlarged.

15. An analytic test strip comprising:
a viewing window;
holding means for storing a reagent or carrier liquid comprising:
(i) a liquid impermeable, deformable blister and
(ii) a liquid impermeable, rupturable diaphragm, wherein the blister and the diaphragm together form a storage chamber for the reagent or carrier liquid;
a layer of absorbent material positioned to receive the reagent or carrier liquid from the storage chamber and to carry the reagent or carrier liquid together with a test substance to said viewing window, wherein a predetermined condition of the test substance is indicated by the color or tone of said layer of absorbent material visible through said viewing window; and
at least one spike formed of said liquid impermeable material and defining an inner surface portion of said blister and extending into the storage chamber toward the diaphragm, wherein the reagent or carrier liquid in the storage chamber is brought into contact with said layer of absorbent material by rupturing the diaphragm with said at least one spike.

16. An analytic test strip according to claim 15 further comprising:
an opening in said test strip, including the diaphragm, to permit the test substance to be contacted with said layer of absorbent material.

17. An analytic test strip according to claim 16, wherein said opening is positioned on said test strip either between the blister and said viewing window or at a location separated from said viewing window by the blister.

18. A test strip according to claim 17, wherein said layer of absorbent material has one or more discreet bands or regions of an absorbed reagent substance positioned on said test strip between said viewing window and both said opening and the blister.

19. A test strip according to claim 16 further comprising:
a cover over said opening, said cover being peelably adhered to said test strip.

20. An analytic test strip comprising:
a viewing window;
holding means for storing a reagent or carrier liquid comprising:

(i) a liquid impermeable, deformable blister and
(ii) a liquid impermeable, rupturable diaphragm, wherein the blister and the diaphragm together form a storage chamber for the reagent or carrier liquid;

a layer of absorbent material positioned to receive the reagent or carrier liquid from the storage chamber and to carry the reagent or carrier liquid together with a test substance to said viewing window, wherein a predetermined condition of the test substance is indicated by the color or tone of said layer of absorbent material visible through said viewing window;

an opening in said test strip, including the diaphragm, to permit the test substance to be contacted with said layer of absorbent material, wherein said opening is positioned on said test strip either between the blister and said viewing window or at a location separated from said viewing window by the blister;

a cover over said opening, said cover being peelably adhered to said test strip;

one or more discreet bands or regions of an absorbed reagent substance positioned on said test strip between said viewing window and both said opening and the blister; and at least one spike formed of said liquid impermeable material and defining an inner surface portion of said blister and extending into the storage chamber toward the diaphragm, wherein the reagent for carrier liquid in the storage chamber is brought into contact with said layer of absorbent material by rupturing the diaphragm with said at least one spike.

\* \* \* \* \*